(12) United States Patent
Rosenthal et al.

(10) Patent No.: US 8,241,042 B2
(45) Date of Patent: Aug. 14, 2012

(54) DYNAMIC PULSE SIMULATOR

(75) Inventors: Richard Rosenthal, Mesa, AZ (US);
Michael A. Schoch, Granite Falls, WA (US); Bryan Hoog, Lake Stevens, WA (US)

(73) Assignee: Fluke Corporation, Everett, WA (US)

( * ) Notice: Subject to any disclaimer, the term of this patent is extended or adjusted under 35 U.S.C. 154(b) by 573 days.

(21) Appl. No.: 12/484,385

(22) Filed: Jun. 15, 2009

(65) Prior Publication Data

US 2010/0316984 A1 Dec. 16, 2010

(51) Int. Cl.
*G09B 23/28* (2006.01)
(52) U.S. Cl. ......................... 434/268; 434/267
(58) Field of Classification Search .................. 434/262, 434/265, 267, 268, 272; 600/301, 485, 501, 600/502; 73/1.57, 866.4
See application file for complete search history.

(56) References Cited

U.S. PATENT DOCUMENTS

| | | | |
|---|---|---|---|
| 2,715,331 A | 8/1955 | Yates et al. | |
| 3,453,861 A | 7/1969 | Levasseur | |
| 3,868,844 A | 3/1975 | Klein | 73/4 R |
| 4,464,123 A | 8/1984 | Glover et al. | 434/268 |
| 5,016,466 A | 5/1991 | Ness et al. | 73/4 R |
| 5,027,641 A | 7/1991 | Costello, Jr. | 73/4 R |
| 5,209,654 A | 5/1993 | Lofsjogard Nilsson et al. | 717/478 |
| 5,284,423 A | 2/1994 | Holdsworth et al. | 417/28 |
| 5,499,906 A | 3/1996 | O'Leary | 417/53 |
| 6,007,342 A * | 12/1999 | Tjolsen | 434/265 |
| 6,205,871 B1 * | 3/2001 | Saloner et al. | 73/866.4 |
| 6,984,212 B1 | 1/2006 | Yang | 600/490 |
| 7,266,986 B2 * | 9/2007 | Shirley et al. | 73/1.57 |
| 7,320,599 B2 * | 1/2008 | Morris | 434/262 |
| 7,510,398 B1 * | 3/2009 | Thornton | 434/262 |
| 2005/0131307 A1 * | 6/2005 | Ruiter et al. | 600/485 |
| 2008/0118901 A1 | 5/2008 | Morris | 434/267 |
| 2010/0075285 A1 * | 3/2010 | Stalling et al. | 434/258 |
| 2010/0291524 A1 * | 11/2010 | Iwasaki et al. | 434/272 |

OTHER PUBLICATIONS

Enoki, Hideo et al., "*A Twist-Type Rubber-Tube Pump*", JSME Series B, vol. 46, No. 1, 2003.

* cited by examiner

*Primary Examiner* — Kurt Fernstrom
(74) *Attorney, Agent, or Firm* — Christensen O'Connor Johnson Kindness PLLC

(57) ABSTRACT

Embodiments of the present invention are directed to a system and method for generating a simulated pulse to be used in combination with a patient monitor. In many embodiments, a pulse is simulated by displacing a volume in a pressurized system. For instance, in one embodiment, the volume in the pressurized system is displaced by rotating a first end of a tube relative to a second end that is held stationary. A portion of the tube collapses due to the twisting causing the volume in the system to decrease. The first end of the tube may be rotated back to its original position causing the volume in the system to return to its original state. This change in volume simulates a pulse.

19 Claims, 4 Drawing Sheets

US 8,241,042 B2

DYNAMIC PULSE SIMULATOR

TECHNICAL FIELD

This invention relates to generating a simulated pulse, and more particularly, one or more embodiments of this invention relate to generating a simulated pulse to be used in combination with a patient monitor.

BACKGROUND OF THE INVENTION

Patient monitors, such as blood pressure monitors, electrocardiogram (ECG) monitors, and heart rate monitors, monitor a patient's health. Patient monitors may be invasive or non-invasive. Non-invasive patient monitors are generally preferred over invasive patient monitors since non-invasive patient monitors may provide a lower health risk to the patient being monitored. Because patient monitors may play a significant role in a patient's health care, it is important that the monitor is functioning properly. For instance, health care professionals may rely on a patient monitor when diagnosing a patient. Therefore it may be critical that the patient monitor is making an accurate reading. To confirm that a patient monitor is functioning properly, patient monitors may be verified and/or tested.

One way to test and verify a patient monitor is by using a pulse generator or simulator. Often, prior art pulse simulators are large and expensive. Furthermore, large pulse simulators are not very portable and are inconvenient for technicians to transport around a hospital to various patient monitors to be tested and/or verified. There is, therefore, a need for less expensive and easily portable pulse simulator for testing patient monitors.

SUMMARY OF THE INVENTION

One or more embodiments of the invention are directed to a system and method for generating a simulated pulse. In one aspect of the invention the pulse simulator includes an actuator having a shaft and a flexible tube. The flexible tube may have a first portion coupled to the shaft and a second portion coupled to a stationary device. The flexible tube may be operable to maintain a pressure above ambient pressure. The actuator may be operable to rotate the shaft and the first portion of the tube in a first direction to cause a portion of the flexible tube to twist and to rotate the shaft and the first portion of the tube in a second direction to cause the flexible tube to straighten.

DETAILED DESCRIPTION OF PREFERRED EMBODIMENTS

Embodiments of the present invention are directed toward patient monitors, and more particularly, one or more embodiments of this invention relate to simulating a pulse, such as a heart beat, to be used in combination with a patient monitor. Certain details are set forth below to provide a sufficient understanding of the embodiments of the invention. However, it will be clear to one skilled in the art that various embodiments of the invention may be practiced without these particular details.

Figure 1:
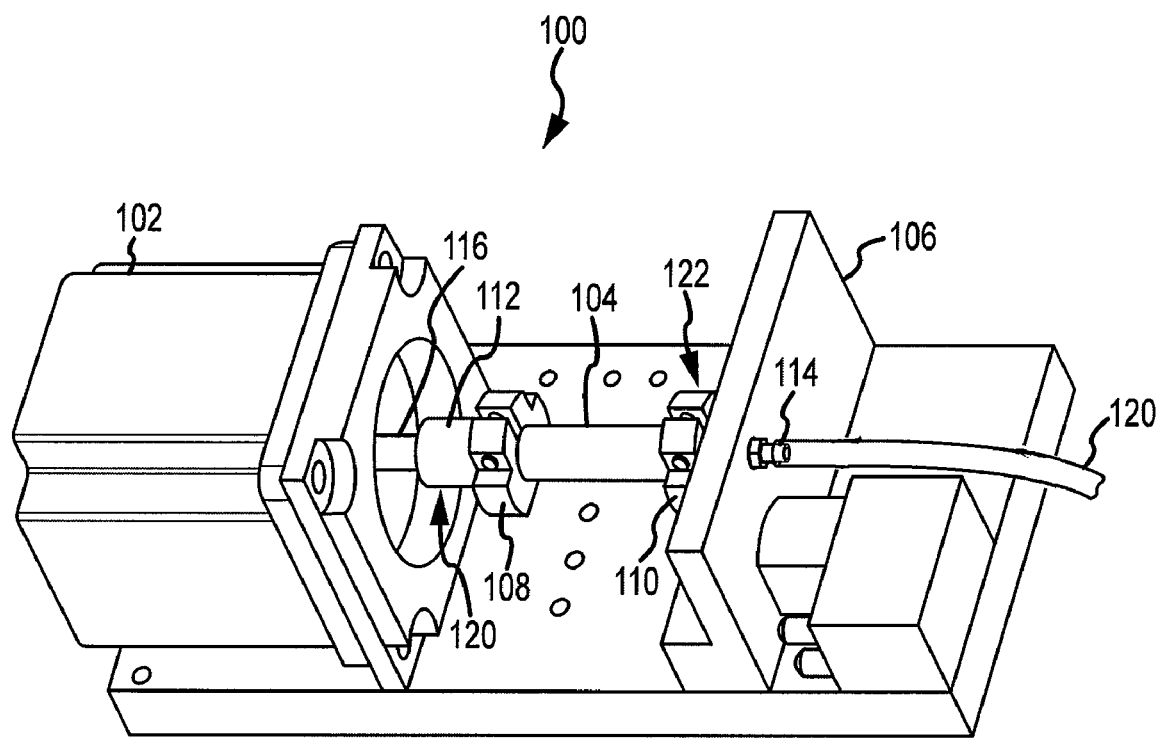
FIG. 1 is an isometric schematic illustration of a dynamic pulse simulator according to one embodiment of the invention.

FIG. 1 is an isometric schematic illustration of a dynamic pulse simulator or generator 100 according to one embodiment of the invention. The dynamic pulse simulator 100 may be used to verify and/or test a patient monitor (not shown). For instance, in one embodiment the dynamic pulse simulator 100 may be used to test a non-invasive blood pressure monitor, ECG monitor, or heart rate monitor. Additionally, the dynamic pulse simulator 100 may be operable to train hospital personnel to use a particular monitor. In many embodiments, the dynamic pulse simulator 100 generates a pneumatic pulse by displacing a volume within a pneumatic system. For instance, a pulse may be generated in a pressurized system, by temporarily increasing the pressure in the system. As will be further explained below, the pressure is temporarily increased by rotating an end of a pressurized tube such that the tube deforms thereby decreasing the volume in the pneumatic system.

The dynamic pulse simulator 100 in FIG. 1 may include an actuator 102, a flexible tube 104, a stationary structure 106, first and second clamps 108 and 110, a coupling 112, and a fitting 114. The actuator 102 may include a shaft 116 extending therefrom. The actuator 102 may be a bi-directional actuator. For instance, the actuator 102 may be operable to alternately rotate the shaft 116 counter clockwise and clockwise. In one embodiment, the actuator 102 is operable to rotate the shaft 116 180 degrees. In one embodiment, the actuator 102 is a rotary stepper motor. The actuator 102 may include a homing device to indicate when the actuator is positioned in a reference position. The homing device may be mechanical or electrical. The homing device may be integral with or separate from the actuator 102. A first end 120 of the flexible tube 104 may be coupled to the shaft 116 extending from the actuator 102 by the coupling 112. A second end 122 of the flexible tube 104 may be held stationary. For instance, the second end 122 of the flexible tube 104 may be coupled to the stationary structure 106 so that the second end 122 of the flexible tube 104 is held stationary. In another embodiment, the second end 122 of the flexible tube 104 may be coupled to the fitting 114. In this embodiment, the fitting 114 is secured to the stationary structure 106 so that the second end 122 of the flexible tube 104 may be held stationary.

The flexible tube 104 may be any tube formed from a flexible material, such as a polymer or elastomer. The tube 104 may be sealed from ambient pressure. In one embodiment, the tube 104 is sealed at the first end 120 and the second end 122 by a hose clamp 108 and 110, respectively. However, any method or device operable to seal the tube 104 from ambient pressure may be used. The second end 122 of the flexible tube 104 may be in fluid communication with the fitting 114. In particular, the second end 122 of the flexible tube 104 may be coupled to a first end of the fitting 114. In one embodiment, the fitting 114 is a barbed fitting. A second end of the fitting 114 may be coupled to a line or hose 120. The hose 120 may be coupled to a device, such as a pump (not shown), operable to pressurize the tube 104 and the hose 120 with a gas, such as air. The hose 120 or another line may also be coupled to the patient monitor. The hose 120 and the tube 104 in combination with the pump create a pneumatic system that may be pneumatically coupled to the patient monitor. In some embodiments, the tube 104 and the hose 120 may be pressurized to a generally static pressure and then the pressure in the system is gradually lowered while pulses are generated.

Figure 2:
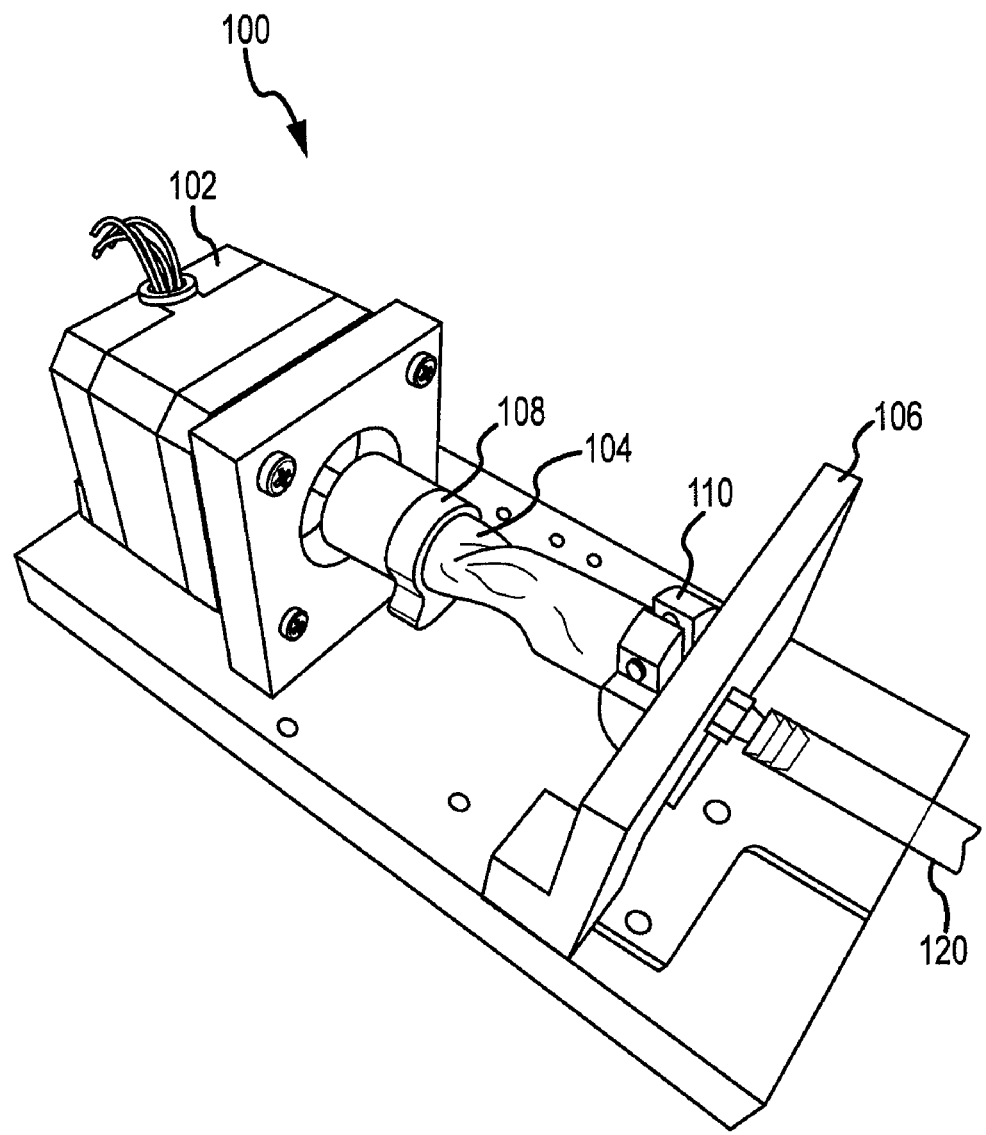
FIG. 2 is an isometric schematic illustration of a dynamic pulse simulator with a first end of a tube rotated according to one embodiment of the invention.

To simulate a pulse, the actuator 102 may rotate the first end 120 of the tube 104 in a first direction. For instance, as an example, the actuator may rotate the first end 120 of the tube 104 180° in a clockwise direction. As will be clear to a person having ordinary skill in the art, the actuator 102 may rotate the first end 120 of the tube 104 to any angle between 0 and 360 degrees and rotate in either the clockwise or counter clockwise direction. FIG. 2 is an isometric schematic illustration of the dynamic pulse simulator 100 showing the first end 120 of the tube 104 rotated according to one embodiment of the invention. In this embodiment, the second end 122 of the tube 104 is held stationary. For instance, in this embodiment the second end 122 of the tube 104 is held stationary by coupling the second end 122 of the tube to the fitting 114, which is secured to the stationary structure 106. As indicated above, the tube 104 is formed from a flexible material. Thus, as is shown in FIG. 2, rotating the first end 120 of the tube 104 in the clockwise direction while the second end 122 of the tube 104 is held stationary twists the tube 104 to cause it to twist or deform. For instance, in this embodiment the first end 120 of the tube 104 rotates so that the tube 104 twists into an hourglass like shape. This twisting decreases the volume of space for the air in the tube 104 and increases the pressure in the system. At this point, the actuator 102 may rotate the first end 120 of the tube 104 in a second direction, such as 180° in a counter clockwise direction. Thus, the tube 104 may untwist back to its original state or to a state in which the tube 104 is at least less twisted than when rotated in the clockwise direction. Untwisting the tube 104 increases the volume of space for the air in the tube 104 and decreases the pressure in the system. The brief increase in pressure in the pneumatic system simulates a pneumatic pulse in the patient monitor to which the pulse simulator 100 is mechanically and pneumatically coupled.

In one embodiment, the actuator 102 is coupled to a controller and a microprocessor. The microprocessor controls the timing of the pulse simulator 100. In particular, the microprocessor controls the pulse simulator 100 to produce pulses at a particular pulse rate and/or frequency to produce the pneumatically simulated pulse. The controller controls the operation of the actuator 102. For instance, the controller may be operable to control the degree of angle the actuator 102 rotates, the speed at which the actuator 102 rotates, the acceleration or deceleration of the actuator 102, and/or how often the actuator 102 rotates in response to signals received from the microprocessor. As will be clear to a person having ordinary skill in the art, these and other variables control the simulated pulse rate.

Figure 3:
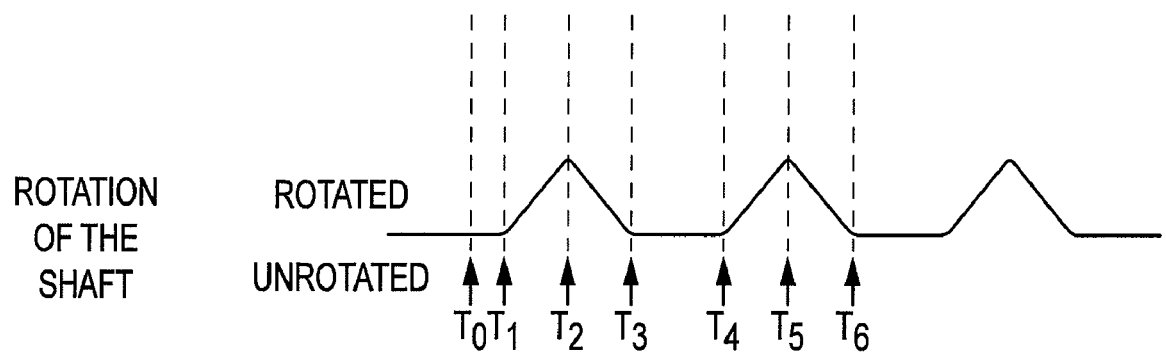
FIG. 3 is a timing diagram illustrating pulses generated by a dynamic pulse simulator according to one embodiment of the invention.

FIG. 3 is a timing diagram illustrating pulses generated by the dynamic pulse simulator 100 shown in FIGS. 1 and 2 according to one embodiment of the invention. At time $T_0$ the shaft 116 and the first end 120 of the tube 104 are unrotated. At time $T_1$ the actuator 102 begins to rotate the shaft 116 and the first end 120 of the tube 104 in a clockwise direction. At time $T_2$ the shaft 116 and the first end 120 of the tube 104 have been rotated 180° in the clockwise direction. As discussed above, this rotation of the first end 120 of the tube 104 while the second end 122 of the tube 122 is held stationary causes the tube 104 to twist and collapse. This deformation increases the pressure in the pneumatic system. Some time after $T_2$ the actuator 102 begins to rotate the shaft 116 and the first end 120 of the tube 104 in a counter clockwise direction. At time $T_3$ the shaft 116 and the first end 120 of the tube 104 have been rotated 180° in the counter clockwise direction. By rotating the first end 120 of the tube 104 back to its original position, the pressure in the system decreases to the original pressure in the system, such as the pressure prior to time $T_1$. As was indicated above, the pressure in the system may by dynamic, such that the pressure in the system is slowly lowered while the pulses are being generated. In that embodiment as will be clear to a person having ordinary skill in the art, the pressure in the system will not decrease to exactly the pressure in the system when the tube is twisted back to its original position. Rather, the pressure in the system will decrease to something slightly less than the original pressure in the system.

The time between $T_1$ and $T_3$ defines a duration of the simulated pulse. At time $T_4$ the actuator 102 again begins rotating the shaft 116 and the first end 120 of the tube 104 in a clockwise direction. The time between $T_3$ and $T_4$ defines an interval between the simulated pulses. At time $T_5$ the shaft 116 and the first end 120 of the tube 104 have been rotated 180° in the clockwise direction. Some time after $T_5$ the actuator 102 again begins to rotate the shaft 116 and the first end 120 of the tube 104 in a counter clockwise direction. At time $T_6$ the shaft 116 and the first end 120 of the tube 104 have been rotated 180° in the counter clockwise direction.

As will be clear to a person having ordinary skill in the art, the microprocessor may be operable to control the duration of the pulse, the magnitude of the pulse, and the interval between each pulse. Additionally, the microprocessor may be operable to control the shape of the pulse. In particular, the microprocessor may be operable to control the speed at which the shaft 116 rotates as a function of time. For instance, if the shaft 116 rotates faster in the first direction than it rotates in the second direction, the pulse may have a steeper slop on the rising edge than on the falling edge. As will be clear to a person having ordinary skill in the art, by changing the rotational speed of the shaft 116 over time, a variety of shaped pulses may be generated.

Figure 4:
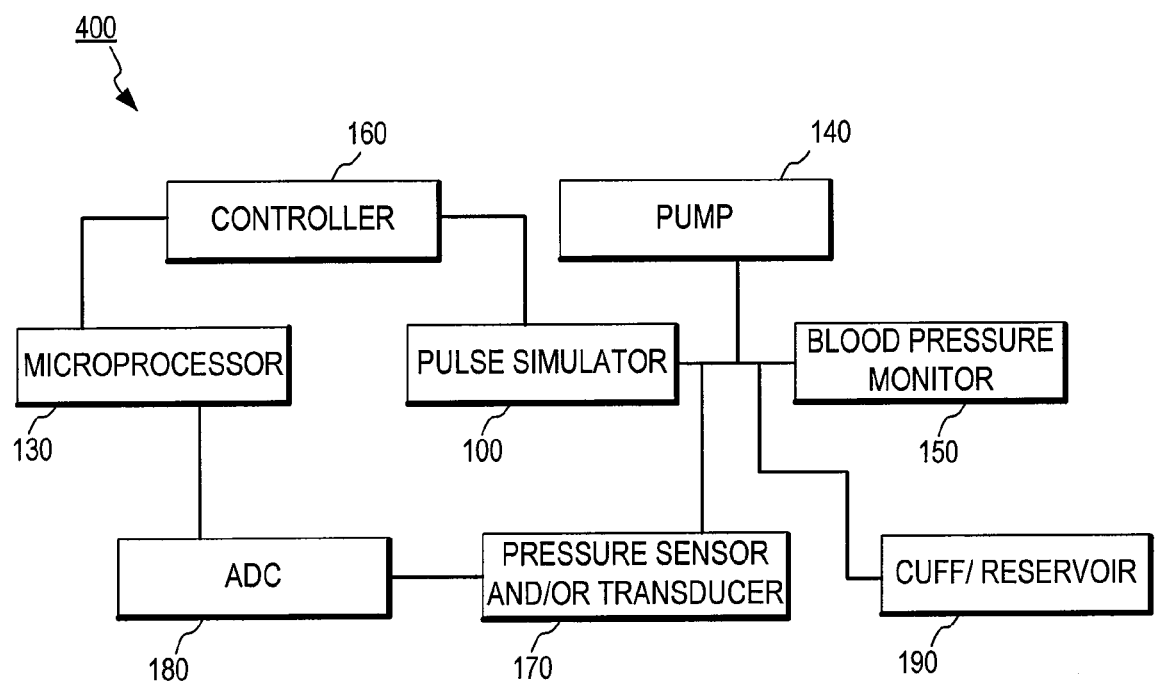
FIG. 4 is a block diagram of a system comprising a pulse simulator according to one embodiment of the invention.

FIG. 4 is a block diagram of a system 400 according to one embodiment of the invention. The system 400 may include a pulse simulator 100, a microprocessor 130, a pump 140, a blood pressure monitor 150, a controller 160, a pressure sensor and/or transducer 170, an analog to digital converter (ADC) 180, and a cuff and/or reservoir 190. The pulse simulator 100 may be the pulse simulator 100 from FIGS. 1 and 2. The microprocessor 130 and the controller 160 are coupled to the pulse simulator 100. The microprocessor 130 may be operable to control the timing of the pulses. The controller 160 may be operable to control the actuator in the pulse simulator 100. The pulse simulator 100 is pneumatically and mechanically coupled to the pump 140 to create a pneumatic system. The pump 140 is operable to pressurize the pulse simulator 100. Additionally, the pulse simulator 100 is pneumatically coupled to the blood pressure monitor 150. In some embodiments, the pump 140, the microprocessor 130, the controller 160, the pressure sensor and/or transducer 170, and ADC converter 180 are provided on a same device as the pulse simulator 100. The system 400 may include a feedback system. In the feedback system, the pressure sensor and/or transducer 170 may be operable to measure the pressure in the system and to provide an analog signal to the ADC 180. The ADC provides a digital signal to the microprocessor 130.

As indicated above, the microprocessor 130 may be operable to control the magnitude, frequency and duration of the simulated pulse. For instance, the rate at which a pulse is generated, such as beats/minute and/or a simulated blood pressure, may be selected as an input to the pulse simulator 100. In particular, the pulse simulator 100 may be set to a particular level so that the pneumatic system generates pneumatically simulated pulses at the particular level set on the pulse simulator. For instance, to test the blood monitor 150 a user may be able to set a pulse simulator to a particular blood pressure level and select a test button to begin a test cycle. Conversely, the rate at which a pulse is generated may be selected as an input to the blood monitor 150.

Although the present invention has been described with reference to the disclosed embodiments, persons skilled in the art will recognize that changes may be made in form and detail without departing from the spirit and scope of the invention. For instance, as will be clear to a person having ordinary skill in the art, the dynamic pulse generator may include a hydraulic system rather than a pneumatic system. For instance, the tube 104 and hose 120 in FIG. 1 may be filled with a liquid, rather than a gas. Thus the tube 104, hose 120 and a pump would create a hydraulic system. The hydraulic system may be coupled to a patient monitor via a pneumatic line. Such modifications are well within the skill of those ordinarily skilled in the art. Accordingly, the invention is not limited except as by the appended claims.

What is claimed is:

1. A pulse simulator, comprising:
   an actuator having a shaft;
   a stationary device positioned a predetermined distance from the actuator; and
   a flexible tube having a length, a first portion coupled to the shaft and a second portion coupled to the stationary device, the flexible tube operable to maintain a pressure above ambient pressure, the actuator operable to rotate the shaft and the first portion of the tube from a first position in a first direction to cause a portion of the flexible tube to deform into a second position and to rotate the shaft and the first portion of the tube in a second direction to cause the flexible tube to straighten and return to the first position, wherein the length of the tube extends the predetermined distance between the actuator and the stationary device when in the first and second positions.

2. The pulse simulator in claim 1 wherein the actuator is coupled to a controller to control the rotation of the shaft and the first end of the tube.

3. The pulse simulator in claim 2 wherein the microprocessor is operable to control at least one of a timing, an angle, and a speed at which the shaft rotates.

4. The pulse simulator in claim 1 wherein the actuator is a rotary stepper motor.

5. The pulse simulator in claim 1 wherein the actuator rotates the shaft and the first end of the tube between 45 degrees and 315 degrees in the first direction.

6. The pulse simulator in claim 1 wherein the microprocessor is operable to control the speed at which the shaft rotates as a function of time.

7. The pulse simulator in claim 1 wherein an angle of rotation in the first direction is substantially equal to an angle of rotation in the second direction.

8. A system for simulating a pulse in a blood monitor, the system comprising:
   a controller;
   an actuator coupled to the controller;
   a pneumatic line removeably coupled to the blood monitor, the pneumatic line having an interior pressurized above ambient pressure; and
   a flexible tube having a length, a first end coupled to the actuator and a second end held stationary, the flexible tube being pneumatically coupled to the pneumatic line, the actuator being operable to twist the first end of the flexible tube in a first direction from a first position to a second position and to twist the first end of the flexible tube in a second direction from the second position to the first position to simulate a pulse in the blood monitor, wherein the length of the tube extends the predetermined distance between the actuator and the stationary device when in the first and second positions.

9. The system of claim 8 wherein the blood monitor is one of a blood pressure monitor or a heart rate monitor.

10. The system of claim 8 wherein twisting the first end of the flexible tube in the first direction causes a portion the tube to twist or deform.

11. The system of claim 8 wherein twisting the first end of the flexible tube in the second direction causes the tube to straighten substantially to its original form.

12. The system of claim 8 wherein the first direction is opposite the second direction.

13. The system of claim 8 further comprising a pump pneumatically coupled to the pneumatic line, the pump being operable to pressurize the interior of the pneumatic line and the flexible tube above ambient pressure.

14. A method of simulating a pulse in a blood pressure monitor, comprising:
   positioning a tube having a length a predetermined distance between an actuator and a stationary device;
   pressurizing the tube to a pressure greater than ambient; and
   twisting a first portion of the tube from a first position to a second position while holding a second portion of the tube stationary and untwisting the first portion of the tube from the second position to the first position while holding the second portion of the tube stationary to simulate a pulse in the blood pressure monitor, wherein the length of the tube extends the predetermined distance between the actuator and the stationary device when in the first and second positions.

15. The method of claim 14 wherein the act of twisting a first portion of the tube while holding a second portion of the tube stationary comprises deforming the tube to decrease the volume of space in the tube and increase the pressure in the pneumatic line.

16. The method of claim 15 wherein untwisting the first portion of the tube while holding a second portion of the tube stationary comprises straightening the tube to increase the volume of space in the tube and decrease the pressure in the pneumatic line.

17. The method of claim 14 the act of twisting a first portion of the tube while holding a second portion of the tube stationary and untwisting the first portion of the tube while holding a second portion of the tube stationary to simulate a pulse in the blood pressure monitor comprises alternately twisting and untwisting at particular intervals.

18. The method of claim 14 wherein the act of pressurizing a tube to a pressure greater than ambient comprises pressurizing the tube to a static pressure greater than ambient and slowly lowering the pressure over time.

19. The method of claim 14 wherein the first portion of the tube is twisted to an angle of rotation that is substantially equal to an angle of rotation in which the first portion of the tube is untwisted.

* * * * *